United States Patent
Cornacchio et al.

(10) Patent No.: US 12,009,080 B2
(45) Date of Patent: Jun. 11, 2024

(54) SYSTEMS AND METHODS FOR INACCURACY DETECTION AND PREVENTION WITHIN PRESCRIPTION INFORMATION

(71) Applicant: CVS Pharmacy Inc., Woonsocket, RI (US)

(72) Inventors: Susan Cornacchio, Ipswich, MA (US); Sarah Marchand, Hopkinton, MA (US); Darlene Molett, Brimfield, MA (US); Vishal Gupta, Westborough, MA (US); Raymond Fogarty, Woonsocket, RI (US); Laurence Drews, Woonsocket, RI (US); Alina Mangiurea, Woonsocket, RI (US); Simon Zahn, Woonsocket, RI (US)

(73) Assignee: CVS Pharmacy, Inc., Woonsocket, RI (US)

( * ) Notice: Subject to any disclaimer, the term of this patent is extended or adjusted under 35 U.S.C. 154(b) by 565 days.

(21) Appl. No.: 17/189,077

(22) Filed: Mar. 1, 2021

(65) Prior Publication Data
US 2021/0272666 A1  Sep. 2, 2021

Related U.S. Application Data

(60) Provisional application No. 62/984,231, filed on Mar. 2, 2020.

(51) Int. Cl.
*G16H 20/10* (2018.01)
*G06F 40/205* (2020.01)
*G06N 20/00* (2019.01)

(52) U.S. Cl.
CPC ........... *G16H 20/10* (2018.01); *G06F 40/205* (2020.01); *G06N 20/00* (2019.01)

(58) Field of Classification Search
CPC ...... G16H 20/10; G16H 70/40; G06F 40/205; G06F 40/279; G06F 40/30; G06N 20/00; G06N 5/025
(Continued)

(56) References Cited

U.S. PATENT DOCUMENTS 7,979,288 B2 * 7/2011 Wilkinson ............. G06Q 10/08
                                                  600/509
8,046,242 B1 * 10/2011 daCosta ................. G16H 10/60
                                                  600/300

(Continued)

OTHER PUBLICATIONS

Xu, Hua, et al. "MedEx: a medication information extraction system for clinical narratives." Journal of the American Medical Informatics Association 17.1 (2010): pp. 19-24. (Year: 2010).*

(Continued)

*Primary Examiner* — Satish Rampuria
(74) *Attorney, Agent, or Firm* — Leydig, Voit & Mayer, Ltd.

(57) ABSTRACT

In some instances, a method for inaccuracy detection and prevention within prescription information is provided. The method comprises: receiving, from a prescription generation system, prescriber prescription information indicating an electronically transmitted medical prescription associated with a patient; converting the electronically transmitted prescription information to a plurality of hierarchical prescription entries based on parsing the electronically transmitted medical prescription associated with the patient; determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries; and based on determining the one or more dispensing inaccura- (Continued)

cies within the plurality of hierarchical prescription entries, providing, to a prescription provider system, provider prescription information indicating the converted electronically transmitted prescription information and the one or more dispensing inaccuracies.

16 Claims, 9 Drawing Sheets

(58) Field of Classification Search
USPC .................................................. 700/90–212
See application file for complete search history.

(56) References Cited

U.S. PATENT DOCUMENTS

| | | | | |
|---|---|---|---|---|
| 10,311,536 | B1* | 6/2019 | Ansari | G06Q 30/04 |
| 10,543,152 | B1* | 1/2020 | Cotter | G05B 15/02 |
| 11,301,630 | B1* | 4/2022 | Markson | G06F 40/30 |
| 11,501,865 | B2* | 11/2022 | Do | G16H 20/13 |
| 11,521,725 | B1* | 12/2022 | Ansari | G16H 20/10 |
| 2004/0059600 | A1* | 3/2004 | Ball | G06Q 10/10 |
| | | | | 705/2 |
| 2006/0136272 | A1* | 6/2006 | Rubsamen | H04L 67/01 |
| | | | | 705/3 |
| 2009/0099870 | A1* | 4/2009 | Wilkinson | G06F 40/274 |
| | | | | 705/3 |
| 2016/0055302 | A1* | 2/2016 | Sellars | G16H 50/20 |
| | | | | 705/3 |
| 2017/0068798 | A1* | 3/2017 | Akinwale | G16H 20/10 |
| 2020/0350064 | A1* | 11/2020 | Karedla | G16H 70/20 |
| 2020/0357499 | A1* | 11/2020 | Do | G16H 40/20 |
| 2022/0384006 | A1* | 12/2022 | Ansari | G16H 20/10 |

OTHER PUBLICATIONS

Bates, David W. "Preventing medication errors: a summary." American Journal of Health-System Pharmacy 64.14_Supplement_9 (2007):pp. S3-S9. (Year: 2007).*

Morimoto, T., et al. "Adverse drug events and medication errors: detection and classification methods." Quality & safety in health care 13.4 (2004): pp. 306-314 (Year: 2004).*

* cited by examiner

| 502 SIG Parse Examples (Most SIGs Do Not Include Every Component) | 504 Delivery Method (Verb) | 506 Dose | 508 Route of Administration (How the drug is administered) | 510 Site of Administration (Where the drug is administered) | 512 Frequency (How often the drug is administered) | 514 Interval (Number of hours between doses) | 516 Time of Day | 518 Duration | 520 Instruction | 522 Indication |
|---|---|---|---|---|---|---|---|---|---|---|
| Apply Topically 2 (Two) Times A Day For 8 Days, Apply To Affected Area(s) For Itch | Apply | | topically | affected areas | Two (2) times a day | | | 8 days | | For itch |
| Inhale 2 Puff by Inhalation Route 2 Times Every Day In The Morning and Evening | Inhale | 2 puffs | by inhalation route | | 2 times every day | | In the morning and evening | | | |
| Inhale 2 Puffs Into The Lungs Every 4 (Four) Hours As Needed | Inhale | 2 puffs | | lungs | | Every 4 (four) hours | | | As needed | |
| Take 1 Tablet By Mouth Every 8 Hours As Needed for Nausea | Take | 1 tablet | by mouth | | | Every 8 hours | | | As needed | For nausea |

| Error | Prescribed Drug Name | Dispensed Label Name | Prescribed GPI_10 | Dispensed _GPI_10 | Logic |
|---|---|---|---|---|---|
| Wrong Drug | Hydrocod/apap tab 5-325mg | Oxycod/apap tab 5-325mg | 6599170210 | 6599060220 | P_GPI_10<>D_GPI_10 |
| Wrong Drug | Tramadol hcl tab 50mg | Trazodone tab 50mg | 6510000510 | 5812008010 | P_GPI_10<>D_GPI_10 |

604

| Error | Prescribed Drug Name | Dispensed Label Name | Prescribed GPI_10 | Dispensed _GPI_10 | Prescribed SIG | Dispensed SIG | Prescribed Time of Day | Dispensed Time of Day | Logic |
|---|---|---|---|---|---|---|---|---|---|
| Wrong SIG Time of Day | Np thyroid tab 90mg | Np thyroid tab 90 mg | 2810005000032 0 | 2810005000032 0 | 1 po oral every morning | Take 1 tablet by mouth every evening | Morning | Evening | P_GPI_CD=D_G PI_CD P_SIG_TIME_O F_DAY<>D_SIG _TIME_OF_DA Y |

606

| Error | Prescribed Drug Name | Dispensed Label Name | Prescribed GPI_10 | Dispensed _GPI_10 | Prescribed SIG | Dispensed SIG | Prescribed Time of Day | Dispensed Time of Day | Logic |
|---|---|---|---|---|---|---|---|---|---|
| Wrong SIG Time of Day | enoxapari n inj 30/0.3ml | enoxapari n inj 30/0.3ml | 8310102010201 2 | 8310102010201 2 | inject 0.3 ml every 12 hours by subcutaneo us route for 7 days | inject 0.3 ml every 12 hours by subcutane ous route for 7 days | For 7.0000 day | For 1.0000 day | P_GPI_CD=D_G PI_CD P_SIG_DURATI ON<>D_SIG_D URATION |

| SIG Examples (Most SIGs Do Not Include Every Component) | Delivery Method (Verb) | Dose | Route of Administration (How the drug is administered) | Site of Administration (Where the drug is administered) | Frequency (How often the drug is administered) | Interval (Number of hours between doses) | Time of Day | Duration | Instruction | Indication | Taper | Taper Time |
|---|---|---|---|---|---|---|---|---|---|---|---|---|
| Apply Topically (Two) 2 Times A Day For 8 Days. Apply To Affected Area(s) For Itch | Apply | | topically | affected areas | Two (2) times a day | | | 8 days | | For itch | | |
| Inhale 2 Puff by Inhalation Route 2 Times Every Day In The Morning and Evening | Inhale | 2 puffs | by inhalation route | | 2 times every day | | In the morning and evening | | | | | |
| Inhale 2 Puffs Into The Lungs Every 4 (Four) Hours As Needed | Inhale | 2 puffs | | lungs | | Every 4 (four) hours | | | As needed | | | |
| Take 1 Tablet By Mouth Every 8 Hours As Needed for Nausea | Take | 1 tablet | by mouth | | | Every 8 hours | | | As needed | For nausea | | |
| Take 2 Tablets On Day 1 Followed By 1 Tablet Daily for 4 Days | Take / Take | 2 tablets / 1 tablets | | | 1 times a day | | | For 4 days | | | Taper 1 / Taper 2 | Day 1 |

FIG. 7

SYSTEMS AND METHODS FOR INACCURACY DETECTION AND PREVENTION WITHIN PRESCRIPTION INFORMATION

CROSS-REFERENCE TO RELATED APPLICATIONS

This patent application claims the benefit of U.S. Provisional Patent Application No. 62/984,231, filed Mar. 2, 2020, which is incorporated by reference herein.

BACKGROUND

Prescribers may provide medical prescriptions electronically to a patient's local pharmacy. The patient may then be alerted when the medication is ready and may then retrieve the medication at their convenience. The medical prescription may indicate directions (i.e., the prescription signa or signetur (SIG.)) associated with the patient taking the medication. For instance, the prescription SIG. may indicate for the patient to take the medication with lunch.

One or more inaccuracies may be introduced between the time the prescriber issues the medical prescription and the time the patient picks up the prescription from the local pharmacy. For example, the prescriber may provide the prescription to an electronic medical record (EMR) system. The prescriber and/or the EMR system may introduce inaccuracies within the medical prescription. The inaccuracies may include the prescriber inputting an incorrect prescription and/or the coding of the EMR system introducing the inaccuracy. For instance, the intent of the medical prescription may be, "take methotrexate once a week for rheumatoid arthritis." However, the prescriber and/or the EMR system may cause the medical prescription to indicate for the patient to "take methotrexate once a day," which may be harmful to the patient.

Traditionally, a system may detect the inaccuracies coming from the prescriber and/or EMR system based on a set of stored pre-defined rules or parameters. For instance, the rules may indicate that a first medication (e.g., medication A) is used for a particular ailment and a second medication (e.g., medication B) is used for another type of ailment. The set of rules may further indicate that a certain dosage is incorrect (e.g., medication A is typically 0.7 grams, but the prescriber inputs 7 grams instead). The system may compare the medical prescription with the set of stored rules and determine the inaccuracy.

Additionally, the network infrastructure between the prescriber's office and the local pharmacy may include additional devices and/or systems. For example, another system (e.g., a dispensing system belonging to an enterprise organization) may actually dispense the prescribed drugs to the patient. The dispensing system may include a back-end server/system and a local pharmacy or other location where the patient may pick up the medication. However, the EMR system and the dispensing system may use different data types or data formats to indicate the prescription SIG. and medication. As such, while the prescription coming from the prescriber and/or EMR system may be correct, dispensing inaccuracies may be introduced within the prescriber's actual prescription during a conversion process from the EMR system to the dispensing system. For example, during the conversion, the prescription SIG. may be changed from taking the medication with lunch to taking the medication with dinner. As such, there exists a need for a technical solution to detect and prevent inaccuracies during the conversion process.

SUMMARY

In one aspect, a method for inaccuracy detection and prevention within prescription information is provided. The method comprises: receiving, from a prescription generation system, prescriber prescription information indicating an electronically transmitted medical prescription associated with a patient; converting the electronically transmitted prescription information to a plurality of hierarchical prescription entries based on parsing the electronically transmitted medical prescription associated with the patient; determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries; and based on determining the one or more dispensing inaccuracies within the plurality of hierarchical prescription entries, providing, to a prescription provider system, provider prescription information indicating the converted electronically transmitted prescription information and the one or more dispensing inaccuracies.

Examples may include one of the following features, or any combination thereof. For instance, in some examples, the method further comprises: receiving, from the prescription provider system, feedback information associated with the one or more inaccuracies; and updating the one or more dispensing parameters based on the feedback information.

In some instances, the determining whether the hierarchical prescription entries includes the one or more dispensing inaccuracies comprises: inputting the hierarchical prescription entries into one or more machine learning datasets to generate data indicating the one or more dispensing inaccuracies.

In some variations, the updating the one or more dispensing parameters comprises updating the one or more machine learning datasets based on the feedback information.

In some examples, the determining whether the hierarchical prescription entries includes one or more dispensing inaccuracies is based on performing a sequential comparative analysis using the hierarchical prescription entries and the rankings associated with the plurality of hierarchical prescription entries.

In some instances, the PDVS comprises a first processor, a second processor, and a third processor. The determining whether the plurality of hierarchical prescription entries includes one or more dispensing inaccuracies comprises determining, by the first processor, whether the plurality of hierarchical prescription entries includes one or more dispensing inaccuracies, wherein the one or more dispensing inaccuracies are introduced by a dispensing system. The method further comprises: determining, by the second processor, whether the plurality of hierarchical entries includes one or more prescriber inaccuracies, wherein the one or more prescriber inaccuracies are introduced by the prescriber generation system; and determining, by the third processor, whether the plurality of hierarchical entries includes one or more financial inaccuracies.

In some variations, the PDVS comprises a decollisioning processor. The method further comprises: determining, by the decollisioning processor, priorities between the one or more dispensing inaccuracies, the one or more prescriber inaccuracies, and the one or more financial inaccuracies; and wherein providing the one or more dispensing inaccuracies is based on the determined priorities.

In some examples, the converting the electronically transmitted prescription information to the plurality of hierarchical prescription entries is based on using a natural language processing (NLP) machine learning algorithm.

In some instances, the prescriber prescription information comprises medication information and a prescription signa. The medication information indicates one or more identifiers associated with a medication for the patient. The prescription signa indicates directions for the patient to take the medication.

In some variations, the converting the electronically transmitted prescription information to the plurality of hierarchical prescription entries comprises generating a first subset of hierarchical prescription entries, of the plurality of hierarchical prescription entries, associated with the medication information and a second subset of the hierarchical entries, of the plurality of hierarchical prescription entries, associated with the prescription signa. The ranking indicates that the first subset of hierarchical prescription entries is ranked higher than the second subset of hierarchical entries.

In some examples, the medication information comprises a national drug code (NDC) and a free-text entry describing the medication. The method further comprises: retrieving, from a database, a database drug description based on the NDC; and comparing whether the database drug description matches the free-text entry describing the medication.

In some instances, the medication information further comprises an RxNorm code. The method further comprises: retrieving, from the database, a database NDC based on the RxNorm code; and comparing the database NDC with the NDC from the medication information.

In some variations, the method further comprises: retrieving, from the database, a generic code number sequence number (GCNSEQNBR) based on the NDC; retrieving, from the database, a second database drug description based on the retrieved GCNSEQNBR; and comparing whether the second database drug description matches the free-text entry describing the medication.

In some examples, the method further comprises: retrieving, from a second database, a generic product identifier (GPI) based on the NDC. The converting the electronically transmitted prescription information to the plurality of hierarchical prescription entries is further based on the GPI.

In another aspect, a system comprises one or more processors; and a non-transitory computer-readable medium having processor-executable instructions stored thereon, wherein the processor-executable instructions, when executed, facilitate: receiving, from a prescription generation system, prescriber prescription information indicating an electronically transmitted medical prescription associated with a patient; converting the electronically transmitted prescription information to a plurality of hierarchical prescription entries based on parsing the electronically transmitted medical prescription associated with the patient; determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries; and based on determining the one or more dispensing inaccuracies within the plurality of hierarchical prescription entries, providing, to a prescription provider system, provider prescription information indicating the converted electronically transmitted prescription information and the one or more dispensing inaccuracies.

Examples may include one of the following features, or any combination thereof. For example, in some instances, the processor-executable instructions, when executed, further facilitate: receiving, from the prescription provider system, feedback information associated with the one or more inaccuracies; and updating the one or more dispensing parameters based on the feedback information.

In some examples, determining whether the hierarchical prescription entries includes the one or more dispensing inaccuracies comprises: inputting the hierarchical prescription entries into one or more machine learning datasets to generate data indicating the one or more dispensing inaccuracies.

In some instances, updating the one or more dispensing parameters comprises updating the one or more machine learning datasets based on the feedback information.

In some variations, determining whether the hierarchical prescription entries includes one or more dispensing inaccuracies is based on performing a sequential comparative analysis using the hierarchical prescription entries and the rankings associated with the plurality of hierarchical prescription entries.

In yet another aspect, a non-transitory computer-readable medium having processor-executable instructions stored thereon, wherein the processor-executable instructions, when executed, facilitate: receiving, from a prescription generation system, prescriber prescription information indicating an electronically transmitted medical prescription associated with a patient; converting the electronically transmitted prescription information to a plurality of hierarchical prescription entries based on parsing the electronically transmitted medical prescription associated with the patient; determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries; and based on determining the one or more dispensing inaccuracies within the plurality of hierarchical prescription entries, providing, to a prescription provider system, provider prescription information indicating the converted electronically transmitted prescription information and the one or more dispensing inaccuracies.

All examples and features mentioned above may be combined in any technically possible way.

BRIEF DESCRIPTION OF THE DRAWINGS

The present application will be described in even greater detail below based on the exemplary figures. The application is not limited to the examples described below. All features described and/or illustrated herein can be used alone or combined in different combinations in examples of the application. The features and advantages of various examples of the present application will become apparent by reading the following detailed description with reference to the attached drawings which illustrate the following:

FIG. 5 shows a data table illustrating exemplary inputs and outputs for the parsing processor in accordance with one or more examples of the present application.

FIG. 6 shows an example of the dispenser inaccuracy determination (DID) processor performing sequential comparative analysis in accordance with one or more examples of the present application.

FIG. 7 shows another data table illustrating exemplary inputs and outputs for the parsing processor in accordance with one or more examples of the present application.

DETAILED DESCRIPTION

Examples of the presented application will now be described more fully hereinafter with reference to the accompanying FIGs., in which some, but not all, examples of the application are shown. Indeed, the application may be embodied in any different forms and should not be construed as limited to the examples set forth herein; rather, these examples are provided so that the disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
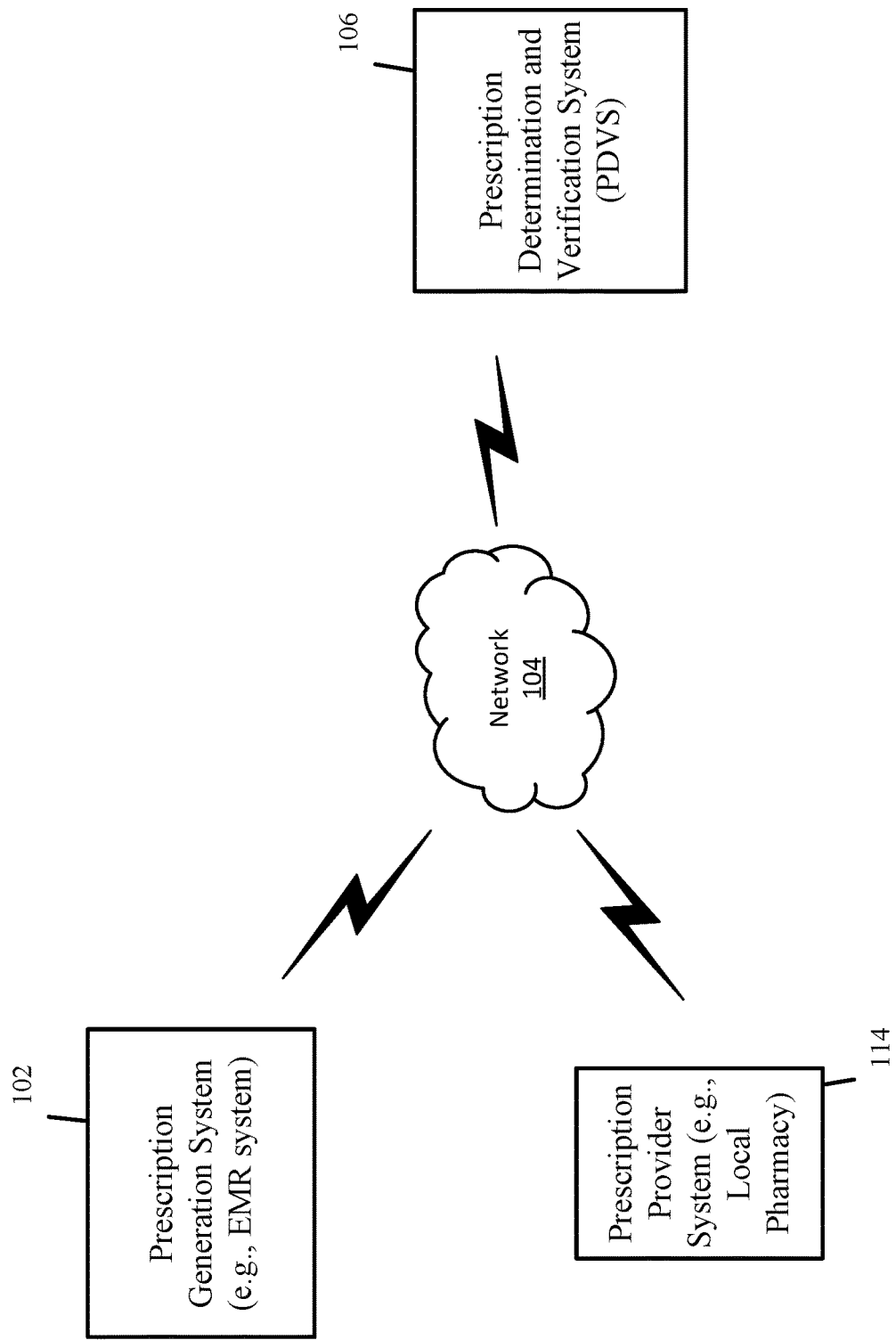
FIG. 1 shows a simplified block diagram depicting an exemplary computing environment in accordance with one or more examples of the present application.

Systems, methods, and computer program products are herein disclosed that verify the prescription information from a prescriber based on determining whether the prescription information includes one or more inaccuracies. FIG. 1 is a simplified block diagram depicting an exemplary environment 100 in accordance with an exemplary embodiment of the present application. The environment 100 includes a prescription generation system 102, a network 104, a prescription determination and verification system (PDVS) 106, and a prescription provider system 114 (e.g., a local pharmacy). As used herein, the systems within the environment 100 include one or more devices, servers, network elements, and/or other types of computing devices.

The systems within the environment 100 may be operatively coupled (e.g., in communication with) other systems within the environment 100 via the network 104. The network 104 may be a global area network (GAN) such as the Internet, a wide area network (WAN), a local area network (LAN), or any other type of network or combination of networks. The network 104 may provide a wireline, wireless, or a combination of wireline and wireless communication between the systems and/or other components within the environment 100.

The prescription generation system 102 includes one or more systems that generate electronically transmitted medical prescriptions and provide the generated medical prescriptions to a dispensing system (e.g., the PDVS 106 and/or the prescription provider system 114). For example, the prescription generation system 102 may include an electronic medical record (EMR) system that includes one or more computing devices, systems, and/or servers.

Additionally, and/or alternatively, the prescription generation system 102 (e.g., EMR system) may include a computing device that a first user such as a prescriber (e.g., a doctor, physician, technician, nurse, and/or another user with prescriptive authority) may use to input a medical prescription for a patient. The prescription generation system 102 may generate prescription information for a patient based on the user input indicating the medical prescription. The medical prescription may indicate one or more medication codes/identifiers (e.g., the National Drug Code (NDC), Orange Book Code, RxNorm Code, free-text description, and so on) and a prescription SIG. (i.e., one or more directions or instructions for the patient to follow in taking the medication). In other words, a first user may prescribe a medical prescription for the patient. The medical information may indicate a medication/drug that is identifiable by the medication code/identifier and a prescription SIG. The prescription generation system 102 may receive user input from the prescriber that indicates this medical prescription for the patient, generate prescription information (e.g., prescriber prescription information) associated with the medical prescription, and provide it to a dispensing system. The generated prescription information (e.g., an electronic prescription (eRx)) includes medication codes/identifiers and the prescription SIG.

The dispensing system may include the PDVS 106 and/or the prescription provider system 114. In some instances, the dispensing system may belong to an enterprise organization that dispenses medications. For instance, the dispensing system may use the prescription/medication information from the EMR system, prepare the medication for the patient based on the prescription information, and provide a physical location/storefront for the patient to obtain the medication.

The PDVS 106 includes one or more processors and/or computing devices that are used for converting the prescription information into hierarchical entries and/or for determining one or more inaccuracies associated with the hierarchical entries. For example, the prescription information from the prescription generation system 102 may be in a first data format (e.g., an extensible markup language (XML) data format). The PDVS 106 may convert the prescription information into a second data format such as hierarchical prescription entries.

After the conversion, the PDVS 106 may determine whether the converted prescription information (e.g., the hierarchical prescription entries) includes one or more inaccuracies. Inaccuracies may include prescriber errors, dispensing errors, and/or financial errors. For example, the inaccuracies may be caused by multiple factors including: information technology companies that support the transmission of electronic prescription orders between prescribers and pharmacies, prescriber errors, and financial discrepancies. For instance, during the conversion of the prescription information into the hierarchical prescription entries, one or more dispensing inaccuracies (e.g., dispensing errors) may be introduced by the dispensing system. Additionally, and/or alternatively, one or more inaccuracies (e.g., prescriber errors) may have already been present in the prescription information from the prescription generation system 102. The PDVS 106 may determine whether the converted prescription information includes any of these inaccuracies (e.g., prescriber and/or dispensing inaccuracies). If so, the PDVS 106 may flag, fix, and/or report these inaccuracies by providing alerts to the prescription provider system 114 and/or by other means. For example, when providing the medical information to the prescription provider system 114 (e.g., the medical information indicating the medication and/or prescription SIG.), the PDVS 106 may further indicate the identified inaccuracies (e.g., provide one or more alerts indicating the one or more inaccuracies) to the prescription provider system 114.

The prescription provider system 114 (e.g., a local pharmacy) includes one or more computing devices that are used for assisting a second user (e.g., a pharmacist, technician, staff member, and/or other worker working at the pharmacy) in providing the prescription to the patient. For example, the prescription provider system 114 may include one or more computing devices with a display. The prescription provider system 114 may receive the prescription information and display the prescription information. Furthermore, the prescription provider system 114 may receive information indicating the inaccuracies including the prescriber inaccuracies, dispensing inaccuracies, and/or financial inaccuracies. The prescription provider system 114 may display an alert, notification, and/or other type of indication that indicates the inaccuracies.

In some examples, the dispensing system (e.g., the PDVS 106, the prescription provider system 114, and/or another system within the dispensing system) first performs a data entry processing step. In the data entry processing step, the dispensing system receives prescription information (e.g., the eRx and/or the original/prescriber prescription information) from the prescription generation system 102 (e.g., EMR system). The dispensing system may convert the received prescription information into a different data format based on manual input (e.g., from the pharmacist, technician, or other user), an automated process (e.g., by using a predefined crosswalk), and/or a combination of both. In the manual process, a first user (e.g., the technician, pharmacist, and other user) may take the received prescription information (e.g., XML data) that is rendered on a computing display and manually enter the prescription information. In some examples, when manually entering the prescription information, the first user may accidentally make a mistake such as introducing a typographical error and/or an inaccuracy into the medication information and/or the SIG. Accordingly, as described below, the PDVS 106 may catch (e.g., determine inaccuracies) and fix (e.g., provide notifications) these mistakes as well as other mistakes from other systems (e.g., the prescription generation system 102).

After, the PDVS 106 may process the information from the data entry processing step by converting it into the hierarchical prescription entries and determine if the prescription information includes one or more inaccuracies such as dispensing inaccuracies, prescriber inaccuracies, and/or financial inaccuracies. If there are inaccuracies, the PDVS 106 may provide an alert indicating the inaccuracies to the data entry workflow station or another computing device at the prescription provider system 114. As will be described below, the PDVS 106 may include multiple processors and each processor may display their own alerts at the prescription provider system 114 (e.g., at the Data Entry workflow station). Additionally, and/or alternatively, a processor such as the decollisioning processor may be used to prioritize the alerts displayed at the prescription provider system 114. A user (e.g., a technician or pharmacist) may maintain and/or alter the prescription information based on the alerts and provide this information back to the PDVS 106. Afterwards, the prescription information may be processed by the PDVS 106 again to determine one or more inaccuracies.

For example, at a subsequent step, a pharmacist at the prescription provider system 114 may perform a data entry verification step. The pharmacist may use a computing device at the prescription provider system 114 (e.g., the Data Entry workflow station and/or another computing device) to confirm whether the converted prescription information matches the actual prescribed prescription from the prescriber. If the initial error remains or if a new error was introduced, the PDVS 106 may again provide applicable alerts to the prescription provider system 114.

In some variations, the prescription provider system 114 may provide feedback information associated with the flagged inaccuracies back to the PDVS 106. For example, the converted prescription may be the same as the prescription by the prescriber (e.g., there should not have been a flagged inaccuracy reported to the prescription provider system 114). The prescription provider system 114 may provide feedback indicating the PDVS 106 should not have provided the flagged inaccuracy. The PDVS 106 may use the feedback information to update one or more parameters that are used to determine the inaccuracies.

The operation and/or functionality of the prescription generation system 102, the prescription provider system 114, and the PDVS 106 will be described in more detail below.

It will be appreciated that the exemplary system depicted in FIG. 1 is merely an example, and that the principles discussed herein may also be applicable to other situations—for example, including other types of devices, systems, and network configurations. For instance, in another configuration, the PDVS 106 may include multiple different computing devices and/or servers that are connected via the network 104. In other words, the PDVS 106 may include multiple devices and/or servers that perform functionalities or operations described herein.

Figure 2:
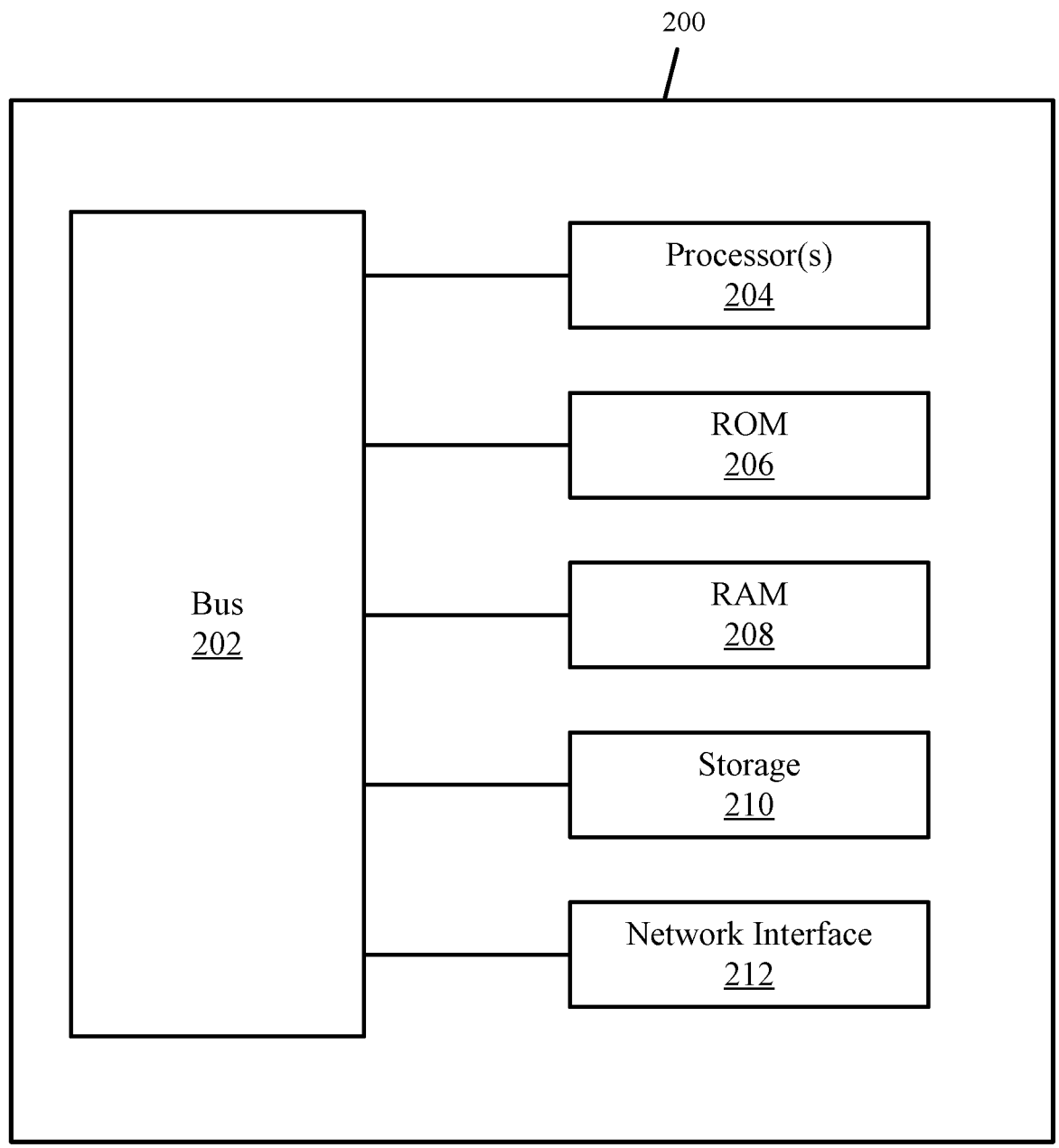
FIG. 2 shows a simplified block diagram of one or more systems within the exemplary environment of FIG. 1.

FIG. 2 is block diagram of an exemplary system within the environment 100 such as the prescription generation system 102, the PDVS 106, and/or the prescription provider system 114). The system 200 includes a processor 204, such as a central processing unit (CPU), controller, unit, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 104. The system 200 may also include a bus 202 that connects the processor 204, ROM 206, RAM 208, storage 210, and/or the network interface 212. The components within the system 200 may use the bus 202 to communicate with each other.

The system 200 of FIG. 2 may be used to implement the methods and systems described herein. For example, as will be explained below, the PDVS 106 may include the components of the system 200 and/or other components such as additional processors, engines, and/or systems.

Figure 3:
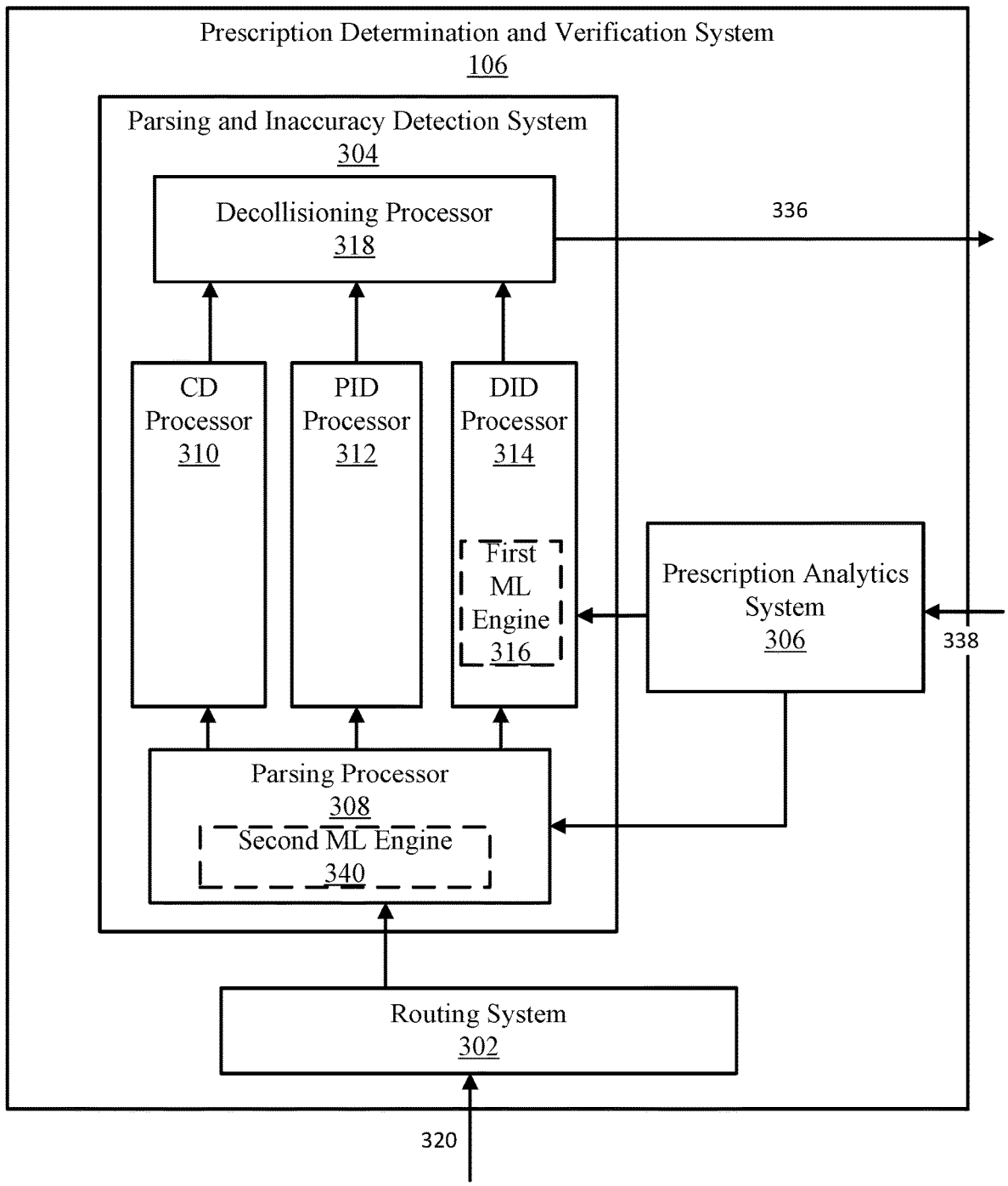
FIG. 3 shows another simplified block diagram depicting an exemplary prescription determination and verification system (PDVS) in accordance with one or more examples of the present application.

FIG. 3 is a block diagram of an exemplary PDVS 106 in accordance with one or more examples of the present application. The PDVS 106 includes a routing system 302, a parsing and inaccuracy detection system 304, and a prescription analytics system 306 (e.g., Enterprise Analytics Platform). The parsing and inaccuracy detection system 304 includes a parsing processor 308 (e.g., a SIG. Parse Processor), a compliance determination (CD) processor 310, a prescriber inaccuracy determination (PID) processor 312, a prevention dispenser inaccuracy determination (DID) processor 314, and a decollisioning processor 318. The DID processor 314 may include a first machine learning (ML) engine 316. When present, the DID processor 314 and/or the parsing processor 308 may use one or more machine learning algorithms and/or artificial intelligence (AI) algorithms to perform one or more of the functions described herein such as determining inaccuracies, which is described below. The parsing processor 308 may include a second ML engine 340. When present, the second ML engine 340 may use one or more machine learning algorithms and/or AI algorithms to perform one or more of the functions described herein such as converting the prescription information into a plurality of hierarchical prescription entries. In some examples, other processors from FIG. 3 (e.g., the PID processor 312, the CD processor 310, and/or the decollisioning processor 318) may also include a machine learning engine and/or use a machine learning algorithm and/or an artificial intelligence (AI) algorithm to expand and refine rules/parameters to determine the inaccuracies (e.g., financial and/or prescriber inaccuracies).

To simplify the discussion, the singular form will be used for all components identified in FIG. 3 when appropriate, but the use of the singular does not limit the discussion to only one of each component. For example, multiple processors may implement functionality attributed to the parsing processor 308 and/or other processors.

While the processors 308, 310, 312, 314, and 318 are shown as separate processors, in some examples, one or more of these processors may be combined together and/or the functionalities of these processors may be implemented by a combined processor and/or computing device. In some variations, the processors 308, 310, 312, 314, and 318 may be implemented as engines, software functions, and/or applications. In other words, the functionalities of the processors 308, 310, 312, 314, and 318 might not be separate physical processors such as CPUs, and may be implemented as software instructions stored in a storage (e.g., memory) and executed by one or more processors, such as the storage 210 and processor(s) 204 in FIG. 2.

In operation, the routing system 302 may receive prescription information 320 from the prescription generation system 102 and/or the prescription provider system 114. For example, as described above, in a data entry step, the prescription information may be converted using an automated process, a manual process, and/or a combination of both. In the automated process, the prescription generation system 102 or another system within the dispensing system may use a predefined cross walk process to process the prescription information from the prescriber. In the manual process, the routing system 302 may receive the converted prescription information from the prescription provider system 114. In other words, in the manual process, a technician and/or pharmacist at the local pharmacy and/or another location may review the prescription information and manually input (using a device associated with the system 114) the relevant information into a format usable by the PDVS 106 and/or the provider system 114 for dispensing the medication. In a combination of the manual and automated process, both of the processes above are used. After processing the information based on the above processes, the routing system 302 may receive the processed information.

In other words, prior to the PDVS 106 initiating the verification process (e.g., performing the data entry verification step), the data entry processing step may be performed. In the data entry processing step, the prescription information (e.g., the eRx) from the prescriber may first be processed (e.g., converted and/or adapted) into a format that the PDVS 106 and/or the prescription provider system 114 can use to dispense the medication. This initial conversion process may be performed by the prescription provider system 114 and/or another system within the dispensing system. For instance, the prescription provider system 114 may receive the prescription information from the prescription generation system 102 and process the prescription information into a data format usable for the PDVS 106. Additionally, and/or alternatively, this initial conversion process may be performed by the prescription generation system 102 (e.g., prior to any of the systems within the dispensing system receiving any information from the prescription generation system 102).

In the manual data entry processing step, the prescription provider system 114 and/or another system may receive user input (e.g., from a technician) indicating the processed prescription information. In the automated data entry processing step, the prescription provider system 114 and/or another system may use an automated method (e.g., a predefined cross walk process) to process the prescription information from the prescriber. In a combination of the manual and automated processing step, the prescription provider system 114 and/or another system may use an automated method for certain components of the prescription information (e.g., the medication code or identifier indicating the actual medication) and the manual process for other components (e.g., the actual prescription SIG.). After the data entry processing step is completed, the prescription provider system 114 and/or another system may provide the processed information and/or additional information (e.g., the original prescription information from the prescriber) to the routing system 302.

As described above, the prescription information (e.g., the eRx) may indicate the medication code/identifiers and a prescription SIG. For instance, the medication code/identifiers may include one or more codes, alphanumerical characters, and/or numerical identifiers such as a national drug code (NDC), representative NDC code (repNDC), an Orange Book Code, and/or an RxNorm Code. The NDC and/or the repNDC is a universal drug identifier with ten or eleven numerical digits in three segments and indicates the drug/medicine, the product code (e.g., Dosage Form and/or strength), and the package code (e.g., total amount).

The prescription SIG. may also be in a data format such as an extensible markup language (XML) data format, JavaScript Object Notation (JSON), or a text data format. For instance, the prescription information may indicate:
 {"messageId":"999999999999",
  "directions": "take 2 capsules (5 mg) 2 times a day by mouth with food for 10 days as needed as for pain and cough",
  "expandedSig":"take 1 tablet (10 mg) 2 times a day by mouth in morning and evening with food for 10 days as needed as for pain/cough",
  "threshold":5}

In some examples, the prescription information received by the dispensing system and from the prescriber may be an eRx. This prescription information may be in XML format and includes medication information (e.g., the medication code/identifiers), the prescription SIG, and/or additional information. The medication information may be presented in two or three ways. First, the medication information may include an NDC and/or repNDC. The NDC is specific and can be representative of the drug that should be dispensed (e.g., a brand name drug), but does not have to be the actual drug dispensed (e.g., a generic named drug may actually be dispensed). Optionally, the medication information may further include an RxNorm Code, which may be included in most eRxs, but not might be included in all. The RxNorm is a codified value created by the National Library of Medicine (NLM), where it may be more general than the NDC, but still specifies a specific drug product. Further, the medication information may include a drug description, which is a free-text field (e.g., actual text from written from the prescriber) that may be what the prescriber is seeing when selecting the medication for the patient. In other words, the drug description may include the actual name of the medication rather than being in coded form such as in the NDC or RxNorm code described above. In some instances, the drug description may be standardized by the prescription generation system 102. In other instances, it might not be standardized.

The prescription SIG. may also be in a free-text field. For instance, the prescriber may prepare the medical prescription to be sent to the pharmacy and may type out the directions for the patient to take the prescriptions. In some instances, the prescriber may use codes and the prescription generation system 102 and/or the dispensing system may convert the codes into text (e.g., the code may be "po" and the dispensing system may convert it to "by mouth").

After receiving the prescription information, the routing system 302 may use a Verification Application Layer to route the prescriber prescription information to various processors and/or engines. For example, the routing system 302 may route the prescriber prescription information to the parsing processor 308. In some examples, the PDVS 106 may be implemented in a cloud computing platform. For example, the cloud computing platform may include one or more physical devices, servers, and/or other computing systems. The cloud computing platform may execute the verification application on a layer such that the verification application hosts the various processors, engines, and/or systems of the PDVS 106 shown on FIG. 3. The verification application may coordinate the data flow between the processors, engines, and/or systems of the PDVS 106 and/or create runtime logs for debugging of the PDVS 106. In such examples, the verification application may include the functionalities of the routing system 302.

The parsing processor 308 (e.g., a SIG parse processor and/or engine) may translate or convert the prescription information so it can be "understood" by inaccuracy detection engines and/or the prescription provider system 114. In other words, the parsing processor 308 may convert the prescription information from a first data format (e.g., the original prescription information and/or the processed prescription information) into a second data format such as a plurality of hierarchical prescription entries. The hierarchical prescription entries may indicate information within the prescription information such as the actual drug identification, the drug form, the drug strength, and the prescription SIG. information.

In other words, the parsing processor 308 may consolidate and/or standardize the two types of information within the prescription information by populating the information into hierarchical prescription entries. For instance, in some examples, the parsing processor 308 may convert the medication information from the prescription information into a first subset of hierarchical prescription entries indicating the actual drug (e.g., the drug name), the drug form (e.g., tablet, pill, liquid, and so on), and the drug strength (e.g., 10 mg).

Furthermore, the parsing processor 308 may convert the prescription SIG. into a second subset of hierarchical prescription entries indicating the directions prescribed by the prescriber. FIG. 5 shows an exemplary data table 500 illustrating the prescription SIGs. 502 and the conversion of these prescription SIGs. 502 into hierarchical prescription entries (e.g., 504 through 522). For example, the prescription SIG. may indicate "apply topically 2 (TWO) times a day for 8 days. Apply to affected area(s) for itch." The parsing processor 308 may convert or translate this prescription SIG. into the hierarchical prescription entries 504-522 as shown using natural language processing (e.g., using a natural language processing (NLP) machine learning or AI algorithm), a custom dictionary, and/or one or more rules/parameters/policies. In other words, the parsing processor 308 may parse through the prescription SIG. and may populate the hierarchical prescription entries with appropriate information from the hierarchical prescription entries. For instance, for the delivery method 504, the parsing processor 308 may parse through the prescription SIG. and determine the verb (e.g., apply) within the prescription SIG. The parsing processing 308 may populate the delivery method hierarchical entry 504 with the verb (e.g., apply). For frequency 512, the parsing processor 308 may parse through and determine any frequency information (e.g., two (2) times a day) and populate this information into the frequency hierarchical entry 512.

FIG. 7 shows another exemplary data table illustrating prescription SIGs. and the conversion of these prescription SIGs. into hierarchical prescription entries. For example, in addition to the hierarchical prescription entries shown in data table 500, FIG. 7 also shows tapering hierarchical entries (e.g., "Taper" and "Taper Time"). The tapering hierarchical entries may indicate prescriptions that involve a series of increasing or decreasing doses of a medication over a period of time (e.g., 3 tablets for the first week, 2 tablets for the second week, and 1 tablet for the third week). The PDVS 106 may convert these prescriptions into hierarchical prescription entries and determine inaccuracies associated with the conversion.

In some instances, the parsing processor 308 might not be able to locate or determine the information necessary to populate certain hierarchical prescription entries. For example, for dose 506, the parsing processor 308 may determine that there is no dose information within the prescription SIG. and might not populate that entry (e.g., leave the entry blank).

In some variations, the PDVS 106 may receive converted information from the prescription provider system 114. For example, a technician may manually input the prescription information into the data entries. In such variations, the parsing processor 308 may receive the data entries from the prescription provider system 114, parse these data entries into hierarchical entries, and provide the hierarchical entries to the processors 310, 312, and/or 314.

The data table 500 and the categories of hierarchical prescription entries 504 through 522 are merely examples and there may be other categories of hierarchical prescription entries.

Additionally, and/or alternatively, the parsing processor 308 may convert the prescription information into the hierarchical prescription entries 504 through 522 using a text, XML, JSON, or another file format that identifies the information. For instance, below is another exemplary output from the parsing processor 308 after the conversion to hierarchical prescription entries:

{"sigDeliveryMethod": "take",
"sigDoseForm": "1.0000 tablet",
"sigDoseStrgh": "10.0000 milligram",
"sigDurMulti": 10.0,
"sigDuration": "for 10.0000 day",
"sigFreqMulti": 2.0,
"sigFrequency": "2.0000 time day",
"sigIndication": "for pain cough",
"sigIndication1": "pain",
"sigIndication2": "cough",
"sigIndication3": " ",
"sigInsMulti": 2,
"sigInstruction": "breakfast dinner",
"sigInstruction1": "dinner",
"sigInstruction2": " ",
"sigInstruction3":
"sigInterval": " ",}

Referring back to FIG. 3, the parsing processor 308 may provide the hierarchical prescription entries to the compliance determination processor 310, the prescriber inaccuracy determination (PID) processor 312, and/or the DID processor 314. The parsing processor 308 may provide all of the hierarchical prescription entries or a portion of the entries to the processors 310, 312, and/or 314. In other words, in some examples, the compliance determination processor 310 might not receive all of the hierarchical prescription entries from the parsing processor 308 and may instead receive only a portion of these entries. Other processors, such as the DID processor 314, may receive all of the hierarchical prescription entries.

The compliance determination processor 310 may determine whether the received hierarchical prescription entries includes one or more financial and/or compliance inaccuracies. For instance, an enterprise organization may authorize payment for a 30 day supply of a medicine. However, based on a financial and/or compliance inaccuracy, the converted prescription information may indicate a 90 day supply of the medicine. The compliance determination processor 310 may determine the financial and/or payer compliance inaccuracy (e.g., 90 days instead of 30 days) and provide the financial inaccuracy to the decollisioning processor 318. In other words, the compliance determination processor 310 increases the data entry quality of the hierarchical prescription entries and drives patient safety outcomes. Furthermore, the compliance determination processor 310 ensures payer finance/contract compliance and reduces pharmacy shrink resulting from incorrect quantity/days supply calculations and SIG. interpretations.

The PID processor 312 may determine whether the received hierarchical prescription entries include one or more prescriber inaccuracies. As described above, the prescriber inaccuracies may include the prescriber inputting an incorrect prescription and/or the coding of the EMR system introducing the inaccuracy. The PID processor 312 may detect prescriber errors based on the relationship between the prescribed medication and the directions. For example, the PID processor 312 may store a plurality of pre-set and/or pre-defined rules associated with particular medications and/or directions. The PID processor 312 may use the pre-set/pre-defined rules to determine whether there is an inaccuracy within the prescription. For instance, a stored rule may indicate that ear drops are to be used in a person's ear. Based on this rule, the PID 312 may determine a prescriber inaccuracy if the eRx indicates that the ear drops are directed to be instilled in the eye. The PID processor 312 may provide the inaccuracy to the decollisioning processor 318.

The DID processor 314 may determine whether the received hierarchical prescription entries includes one or more dispensing inaccuracies based on comparing the hierarchical prescription entries with the prescription information using one or more dispensing parameters (e.g., rules and/or policies). In other words, the DID processor 314 may detect inaccuracies that have already occurred (e.g., perform a retrospective review to measure dispensed prescription accuracy) and/or prevent inaccuracies from occurring (e.g., real time alerting about potential dispensing errors). For instance, the DID processor 314 may perform a comparative analysis between the prescription information and the hierarchical prescription entries to determine whether the one or more dispensing inaccuracies has occurred.

Additionally, and/or alternatively, the comparative analysis may be retrospective. In other words, the DID processor 314 may perform a comparative analysis between the prescription information for multiple different patients and prescriptions and the hierarchical prescription entries associated with these patients and prescriptions to determine whether the one or more dispensing inaccuracies has occurred.

Additionally, and/or alternatively, the comparative analysis may be performed substantively in real-time and/or prior to the patient obtaining the medication. In other words, the DID processor 314 may perform comparative analysis and upon determining one or more dispensing inaccuracies, the DID processor 314 may provide an indication (e.g., alert) to the pharmacists and/or technicians during the dispensing workflow such that the pharmacists and/or technicians may be able to correct prior to the medication reaching the patient.

The DID processor 314 may store the data generated from the comparative analysis in a database.

In other words, in some instances, the PID processor 312 may determine, using a set of pre-defined rules, inaccuracies from the prescription generation system 102 such as when the prescriber inputs a prescription that is incorrect. For example, the set of rules may indicate that medication A is used for a particular ailment and medication B is used for another type of ailment. The set of rules may further indicate that a certain dosage is incorrect (e.g., medication A is typically 0.7 grams, but the prescriber inputs 7 grams instead). For example, the prescriber may decide to prescribe a particular medication (e.g., medication A) for a patient including a drug form, drug use, and strength. However, when inputting the information into a computing device of the prescription generation system 102, the prescriber may accidentally input a wrong medication (e.g., medication B) with a similar name. The PID processor 312 may determine the inaccuracy based on the difference in their names and/or uses. For instance, the PID processor 312 may retrieve the set of rules from memory and compare these rules with the prescription. Based on at least one of the rules indicating that the prescriber is incorrect, the PID processor 312 may flag the prescription information as having an inaccuracy. In other words, the PID processor 312 may determine the prescriber inaccuracy due to incompatibility with the prescriptions (e.g., the medication B may be used for itches, but the prescriber has prescribed it for blood pressure control (i.e., the actual drug use for medication A)). Additionally, and/or alternatively, the coding from the EMR system of the prescription generation system 102 may further generate a prescriber inaccuracy.

On the other hand, the DID processor 314 may determine inaccuracies (e.g., dispensing inaccuracies) based on a comparison between the hierarchical entries and the original prescription information (e.g., the eRx) from the prescriber. For example, the prescriber might not have made a mistake when issuing the prescription, but during the data entry processing step described above (e.g., automated process, the manual process, and/or the combination process), an inaccuracy may have been introduced. To put it another way, in some examples, after receiving the prescription information, a technician at the prescription provider system 114 may manually input the prescription information into a format that is suitable for the dispensing system to be able to dispense the medication. The technician may have entered an inaccuracy such as introducing a typographical error while manually inputting the prescription information. Accordingly, during the data entry verification step, the parsing processor 308 may parse through both the original prescription information from the prescriber as well as the new prescription information that the technician entered and use both of the prescription information to generate the hierarchical prescription entries. The DID processor 314 may compare the hierarchical prescription entries for the new and original prescription information to determine whether there has been an inaccuracy that was introduced during the data entry processing step. In other words, the PID processor 312 may be determining prescriber inaccuracies based on using a set of pre-defined rules whereas the DID processor 314 may be determining the dispensing inaccuracies based on comparing the original prescription information with new prescription information from the data entry processing step.

In some examples, the dispensing parameters may indicate to perform a sequential approach for analysis. For instance, each of the hierarchical prescription entries may have an associated hierarchical ranking. The DID processor 314 may perform the comparative analysis based on the associated hierarchical rankings. For example, the actual drug hierarchical prescription entry (e.g., drug name) may have a higher associated rank than the drug strength hierarchical prescription entry. The drug strength hierarchical prescription entry and/or the actual drug hierarchical prescription entry may have higher associated rankings than a prescription SIG. hierarchical prescription entry such as the delivery method hierarchical entry 504. The DID processor 314 may sequentially perform the comparative analysis based on their associated hierarchical rankings (e.g., perform the comparative analysis in order).

The exemplary table below (e.g., Table 1) shows the hierarchical entries with their associated rankings. Furthermore, as shown below, a single hierarchical entry (e.g., SIG. Time of Day) may be associated with two or more types of error categories (e.g., wrong SIG time of Day and/or Missing Time of Day).

TABLE 1

| Processor | Hierarchical Ranking | Hierarchical Entry | Error Category |
|---|---|---|---|
| DID | 1 | Actual Drug | Wrong Drug |
| DID | 2 | Drug Form | Wrong Drug Form |
| DID | 3 | Drug Strength | Wrong Drug Strength |
| DID | 4 | SIG Dose | Wrong SIG Dose |
| DID | 5 | SIG Missing Dose | Wrong SIG Missing Dose |
| DID | 6 | SIG Frequency | Wrong SIG Frequency |
| DID | 7 | SIG Missing Frequency | Wrong SIG Missing Frequency |
| DID | 8 | SIG Route | Wrong SIG Route |
| DID | 9 | SIG Route | Wrong SIG Missing Route |
| DID | 10 | SIG Time of Day | Wrong SIG Time of Day |
| DID | 11 | SIG Time of Day | Wrong SIG Missing Time of Day |
| DID | 12 | SIG Instruction | Wrong SIG Instruction |
| DID | 13 | SIG Instruction | Wrong SIG Missing Instruction |
| DID | 14 | SIG Duration | Wrong SIG Duration |
| DID | 15 | SIG Duration | Wrong SIG Missing Duration |
| DID | 16 | SIG Pro re nata (PRN) | Wrong SIG Missing PRN |
| DID | 17 | SIG Left Quick Code | Wrong SIG Left Quick Code |
| DID | 18 | SIG Indication | Wrong SIG Indication |
| DID | 19 | SIG Indication | Wrong SIG Missing Indication |

Table 1 above is merely an example and other hierarchical entries may be included. Additionally, in other examples, the hierarchical entries may be associated with different hierarchical rankings.

The exemplary table below (e.g., Table 2) shows the input attributes to the DID processor 314 and the outputs from the DID processor 314. As shown, the directions, product code, product quality, NDC dispensed drug, and expanded SIG. are input into the DID processor 314. The DID processor 314 performs comparative analysis as described above and provides a DID inaccuracy and an associated score.

TABLE 2

| Input Attributes for DID Processor | | | | | Output of DID Processor | |
|---|---|---|---|---|---|---|
| DIRECTIONS | PRODUCT_CODE | PRODUCT_QUALITY | NDC_DISPENSED_DRUG | EXPANDED_SIG | DID_ERROR | score |
| 1 tablet by mouth in morning with breakfast | 00378110501 | ND | 60505014101 | 1 tablet by mouth in morning with lunch | Wrong SIG Instruction | 52 |
| 75 mg po bedtime as needed for insomnia | 00378267501 | ND | 70710122801 | take 1 tablet by mouth at bedtime | Wrong SIG Missing PRN | 52 |

TABLE 2-continued

| Input Attributes for DID Processor | | | | | Output of DID Processor | |
| --- | --- | --- | --- | --- | --- | --- |
| DIRECTIONS | PRODUCT_CODE | PRODUCT_QUALITY | NDC_DISPENSED_DRUG | EXPANDED_SIG | DID_ERROR | score |
| 4 drops 2× daily in left ear | 00065853302 | ND | 60505036301 | instill 10 drops into left ear twice a day for 7 days | Wrong Drug | 3 |
| one tablet twice a day for 10 days | 00143211205 | ND | 24658031205 | take 1 tablet by mouth twice a day | Wrong SIG Missing Duration | 0 |
| 2 tab oral daily × 5 days | 00054001825 | ND | 00054001829 | take 2 tablets by mouth for 5 days | Wrong SIG Missing Frequency | 0 |
| take 1 tablet by mouth every day for cholesterol | 00093505698 | ND | 00378395077 | take 1 tablet by mouth every day | Wrong SIG Missing Indication | 0 |
| 1 tablet bid for 7 days | 49708014601 | ND | 65862042005 | bid'f7d | Wrong SIG Left Quick Code | 0 |
| take 1 tab po bid × 5 days with food | 00591544305 | ND | 00054001825 | take 1 tablet by mouth twice a day for 5 days | Wrong SIG Missing Instruction | 0 |
| 2 tablets once a day orally 30 day(s) | 51660075331 | ND | 51672213108 | take 2 teaspoonfuls by mouth every day | Wrong Drug Form | 3 |
| take 2 tablet(s) every day by oral route for 5 days. | 00054001825 | ND | 00054001829 | take 3 tablets by mouth every day for 5 days | Wrong SIG Dose | 3 |
| 1 gtt ou qid × 7-10 days | 00998063006 | ND | 24208083060 | put 1 drop by mouth 4 times a day for 7 to 10 days | Wrong SIG Route | 0 |
| 4 drops in affected ear(s) 4 times daily for 7-10 days. | 24208063110 | ND | 24208063110 | instill 4 drops 4 times a day for 7 to 10 days | Wrong SIG Missing Route | 0 |
| 1 cap(s) orally once a day (at bedtime) × 30 days | 52427028701 | ND | 47781030701 | take 1 capsule by mouth every day | Wrong SIG Missing Time of Day | 0 |
| 1 tablet at bedtime | 71399054001 | ND | 00378395177 | take 1 tablet by mouth everyday at bedtime | Wrong Drug Strength | 3 |

For example, referring to Table 2 above, the DID processor 314 may compare the information from the first three columns (e.g., "DIRECTIONS", "PRODUCT_CODE", and/or "PRODUCT-QUALITY") associated with the original prescription information from the prescriber with the next two columns (e.g., "NDC_DISPENSED_DRUG" AND "EXPANDED-SIG") associated with the new prescription information from the data entry processing step. Based on the comparison, the DID processor 314 may determine whether there is an inaccuracy, which is shown in the "DID_ERROR" and "score" columns. In some examples, the DID processor 314 may compare the first and fifth columns (e.g., the "DIRECTIONS" column with the "EXPANDED_SIG" column) to determine whether there is an inaccuracy within the prescription (e.g., SIG.). The DID processor 314 may further compare the second and fourth columns (e.g., the "PRODUCT_CODE" and "NDC_DISPENSED_DRUG" columns) to determine whether there is an inaccuracy for the actual drug or medication being dispensed. Based on these comparisons, the DID processor 314 may provide the output such as the inaccuracy (e.g., the "DID_ERROR") and/or the score.

Table 2 above is merely an example and the DID processor 314 may receive additional inputs, provide additional outputs, and/or may be configured to determine the dispensing inaccuracies differently.

In some variations, the DID processor 314 may determine more than one dispensing inaccuracy within the hierarchical prescription entries for the prescription. In other variations, during the sequential analysis, the DID processor 314 may determine a dispensing inaccuracy and stop performing the comparative analysis for the rest of the hierarchical prescription entries. For example, if the DID processor 314 determines the drug form is incorrect, the DID processor 314 may stop performing the comparative analysis for the rest of the hierarchical prescription entries (e.g., the entries associated with rankings 3-19 from Table 1 are not performed).

FIG. 6 shows an example of the DID processor 314 performing the sequential comparative analysis. For example, in analysis 602, the DID processor 314 determines the prescribed drug is incorrect (e.g., the prescribed NDC is different from the dispensed NDC) and stops the analysis. In analysis 604, the DID processor 314 performs the comparative analysis until it determines the time of day is incorrect. In analysis 606, the DID processor 314 performs the comparative analysis until it determines the prescribed prescription is incorrect.

Referring back to FIG. 3, after the processors 310, 312, and 314 performs their analysis, the processors 310, 312, and/or 314 may provide the results to the decollisioning processor 318. The decollisioning processor 318 may manage overlapping alerts/notices indicating the one or more inaccuracies (e.g., financial inaccuracies, dispensing inaccuracies, and/or prescriber inaccuracies). The decollisioning processor 318 may provide provider prescription information 336 indicating the alerts/notices to the prescription provider system 114.

For example, the decollisioning processor 318 may prioritize alerts from certain processors over others. For instance, the decollisioning processor 318 may prioritize the alerts from the DID processor 314 over the alerts from the compliance determination processor 310. Additionally, and/or alternatively, the decollisioning processor 318 may suppress some alerts (e.g., alerts from the compliance determination processor 310).

In other words, the decollisioning processor 318 prioritizes inaccuracy/error alerts from the processors 310, 312, and/or 314 based on the criticality of the error and also may add enrichment data (metadata) such as alert queue details, soft/hard stops, prescription attributes to highlight and custom error text message. For example, the decollisioning processor 318 may prioritize and generate the alerts to be displayed at the prescription provider system 114.

After providing the provider prescription information 336 indicating the alerts/notices of the determined inaccuracies to the prescription provider system 114, the prescription provider system 114 may display the alerts/notices. The pharmacist, technician, and/or other worker at the local pharmacy may use the displayed alerts/notices to correct the inaccuracy in the medical prescription.

In some variations, the prescription provider system 114 may provide feedback information 338 to the PDVS 106. For example, the prescription provider system 114 may provide information 338 indicating that the provider prescription information 336 was ignored and there should not have been an alert regarding the inaccuracies (e.g., the prescription information from the prescriber was correct and the flagged inaccuracy was determined incorrectly). Additionally, and/or alternatively, the prescription provider system 114 may provide information 338 indicating that the provider prescription information 336 was kept (e.g., the prescription information from the prescriber was incorrect, the technician fixed the inaccuracy during the data entry processing step, and the flagged inaccuracy was determined correctly).

The prescription analytics system 306 (e.g., Enterprise Analytics Platform) may receive the feedback information 338. Based on the feedback information, the prescription analytics system 306 may update the one or more parameters. For example, as mentioned above the DID processor 314 may use one or more error dispensing parameters to determine the one or more inaccuracies. The one or more error dispensing parameters may be stored in the prescription analytics system 306. In other words, the prescription analytics system 306 may be and/or include a repository that stores the DID rules (e.g., parameters). Additionally, and/or alternatively, the prescription analytics system 306 may also store rules and parameters for the compliance determination processor 310 and/or the prescriber inaccuracy determination processor 312. The prescription analytics system 306 may retrieve the rules/parameters and update them based on the feedback information 338.

In some examples, the DID processor 314 includes a first ML engine 316. In other words, the DID processor 314 may use machine learning to determine whether the hierarchical prescription entries includes the one or more inaccuracies. For example, after converting the hierarchical prescription entries, the DID processor 314 may use one or more machine learning datasets to determine whether the hierarchical prescription entries includes the one or more inaccuracies. The prescription analytics system 306 may train the first ML engine 316 based on feedback information 338 and/or additional information.

In some instances, by using the machine learning database, the DID processor 314 may address the tail (e.g., the approximately 75% of unique prescription SIGs. that appear only once in a while), categorize "unknown tokens" (e.g., words that haven't been categorized for national language processing), address spell check limitations/missing spaces, perceive similarities among unique prescription SIGs. and consolidate them into groups, parse lengthy, complicated prescriber directions, and/or refine and grow the DID processor's 314 rules/parameters through ongoing analysis of the feedback information 338.

In some variations, the DID processor 314 (e.g., the prescription analytics system 306) may use the feedback information 338 to update and/or train the machine learning dataset. In other words, the pharmacist and/or technician may provide feedback to the DID processor 314 and/or the prescription analytics system 306. The DID processor 314 and/or the prescription analytics system 306 may use the feedback to update/train the machine learning dataset by providing confidence thresholds for the generated alerts.

In some examples, the ML engines 316 and/or 340 may employ advanced natural language processing (NLP) techniques, supervised ML techniques, deep learning ML techniques, and/or unsupervised ML techniques. For example, the second ML engine 340 may use an advanced NLP technique such as a comprehensive language model or dataset, which is able to parse the SIG. token with an associated confidence score. The second ML engine 340 may utilize data (e.g., the disposition data) from the prescription analytics system 306 to improve the SIG parse confidence score over time. The disposition data may indicate the pharmacist/technician's response to the alert indicating the inaccuracy. For example, the disposition data may indicate whether the pharmacist/technician ignored, adopted, or rejected the alert. In other words, the disposition data may indicate whether the pharmacist selected "Fill AS IS" option during the verification process.

In some variations, the first ML engine 316 may use supervised classification techniques trained using data (e.g., disposition data) to refine an existing ruleset and apply these rules to a broader set of prescriptions with similar attributes and features. The prescription analytics system 306 may employ a retraining model to improve the alert confidence score over time for the DID processor 314 such that it leads to lesser false positives.

In some instances, the first ML engine 316 may use unsupervised ML techniques such as anomaly detection and outlier detection techniques to identify new inaccuracy categories and rules sets in an automated fashion. The prescription analytics system 306 may use data (e.g., disposition data) and user input indicating a manual review of high frequency alerts by a team to improve the new error accuracy rate overtime.

In some variations, the first ML engine 316 is the output from training the machine learning (ML)/artificial intelligence (AI) algorithms using the disposition data. For example, the prescription analytics system 306 uses the disposition data to train the ML/AI algorithms. Then, the prescription analytics system 306 provides the output (e.g., updated rules/parameters/the first ML engine 316) from the ML/AI algorithms to the DID processor 314. The DID processor 314 uses the first ML engine 316 to identify dispensing inaccuracies within the hierarchical prescription entries (e.g., the medication information and the prescription SIG.). Similarly, the prescription analytics system 306 uses the disposition data to train the ML/AI algorithms for the other processors (e.g., the PID processor 312, the CD processor 310, and/or the decollisioning processor 318). The other processors may use the outputs from the ML/AI algorithms to determine and/or prioritize the inaccuracies (e.g., the prescriber inaccuracies and/or the financial inaccuracies).

It will be appreciated that the exemplary system depicted in FIG. 3 is merely an example, and that the principles discussed herein may also be applicable to other situations— for example, including other types of devices, processors, engines, and/or systems. For instance, as explained above, the functionalities of the processors 308, 310, 312, 314, and 318 may be implemented by software instructions, one or more combined processors, and/or one or more computing devices.

Figure 4:
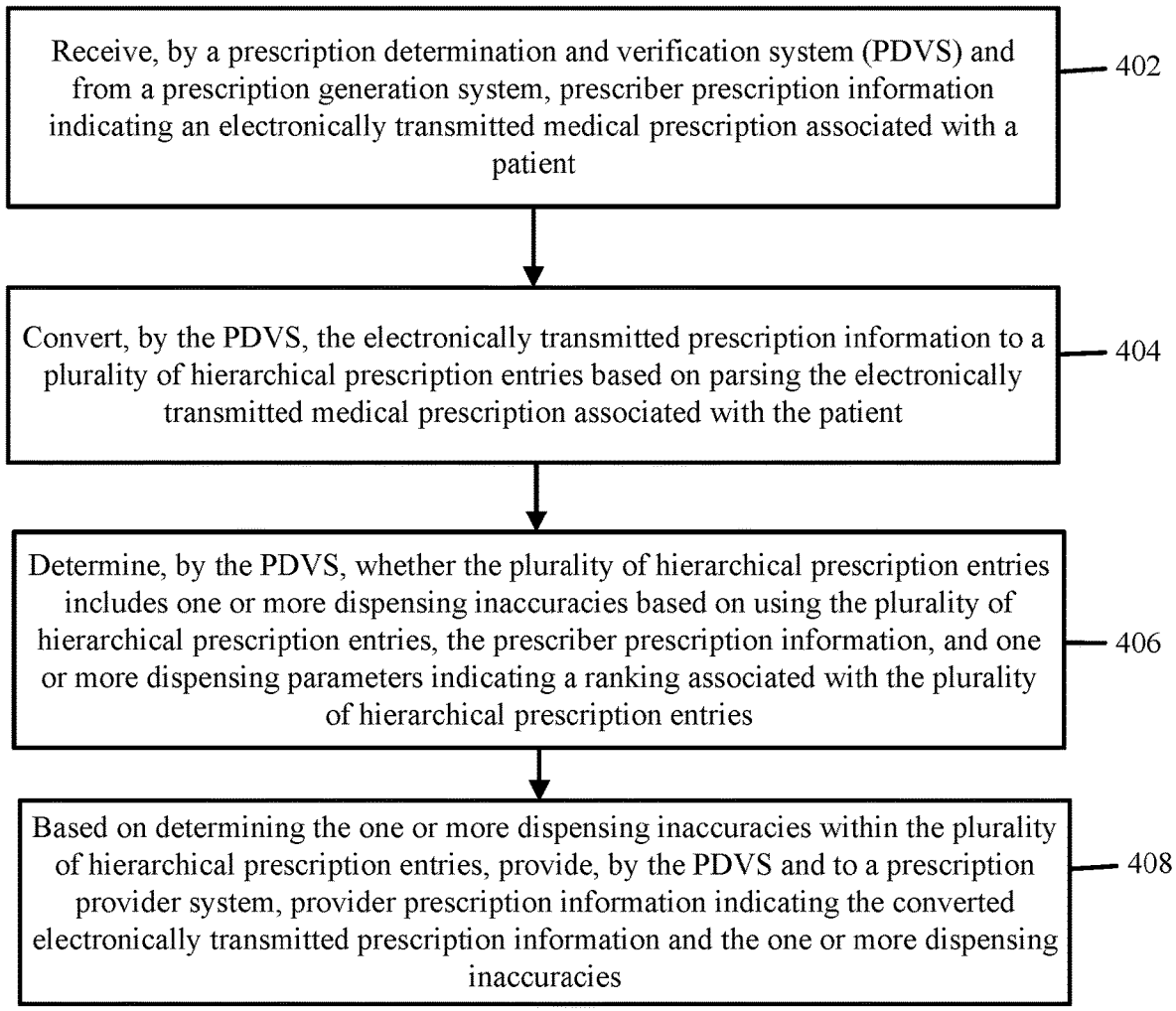
FIG. 4 shows a flowchart illustrating an exemplary process for inaccuracy detection and prevention within prescription information in accordance with one or more examples of the present application.

FIG. 4 is an exemplary flowchart illustrating an exemplary process 400 for inaccuracy detection and prevention within prescription information in accordance with one or more examples of the present application. The process 400 may be performed by the environment 100 and the exemplary PDVS 106 shown in FIG. 3; however, it will be recognized that any suitable environment and system may be used and that any of the following blocks may be performed in any suitable order.

In operation, at block 402, the PDVS 106 may receive, from a prescription generation system 102, prescription information indicating an electronically transmitted medical prescription associated with a patient. At block 404, the PDVS 106 may convert the electronically transmitted prescription information to a plurality of hierarchical prescription entries based on parsing the electronically transmitted medical prescription associated with the patient. At block 406, the PDVS 106 may determine whether the hierarchical prescription entries includes one or more dispensing inaccuracies based on using the hierarchical prescription entries, the prescription information, and one more dispensing parameters indicating a ranking associated with the plurality of hierarchical prescription entries. At block 408, based on determining the one or more dispensing inaccuracies from the hierarchical prescription entries, the PDVS 106 provides, to the prescription provider system 114, provider prescription information indicating the converted electronically transmitted prescription information and the one or more dispensing inaccuracies.

Figure 8A:
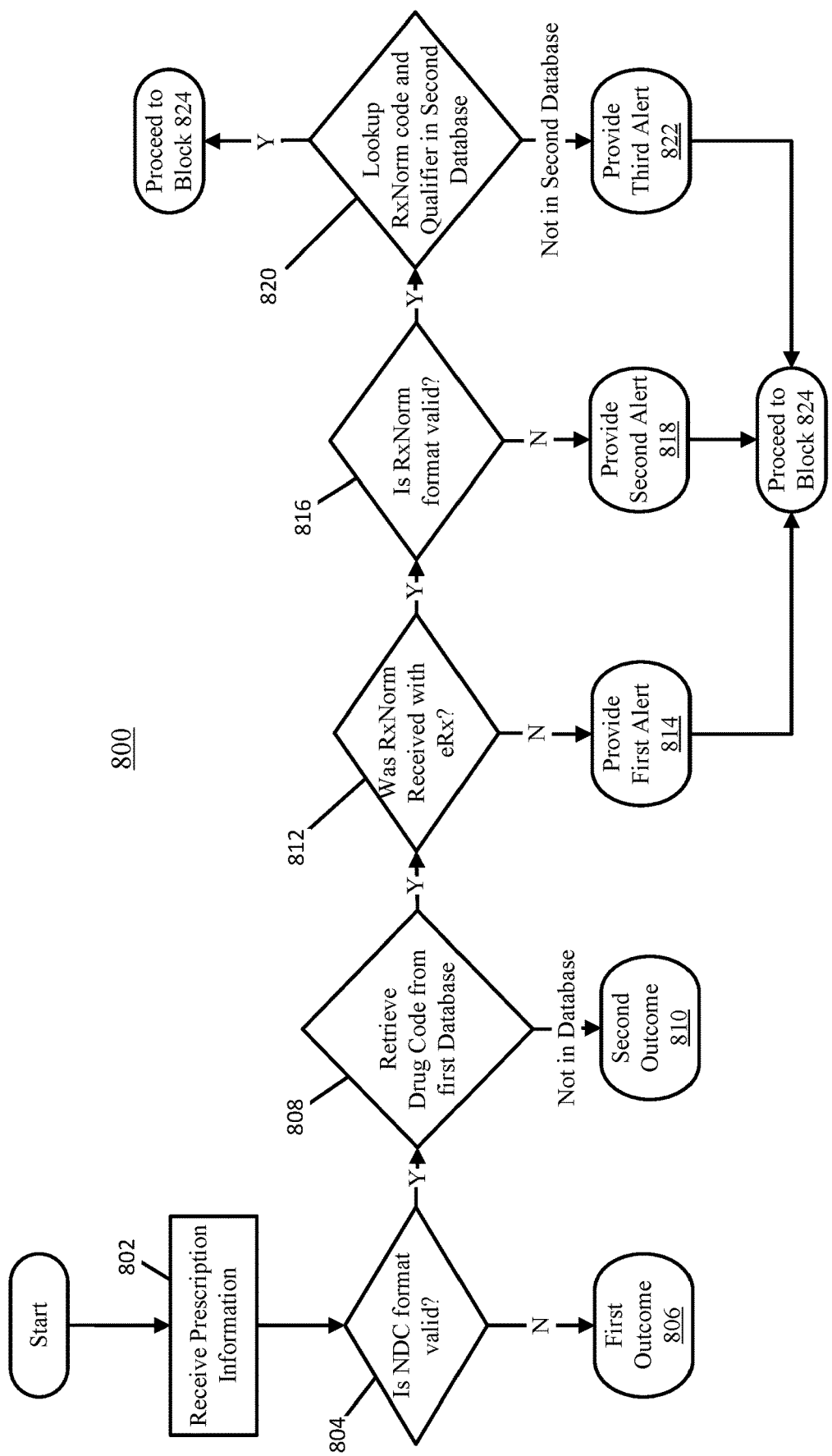
FIGS. 8A and 8B show a flowchart illustrating another exemplary process for inaccuracy detection and prevention within the prescription information in accordance with one or more examples of the present application.
Figure 8B:
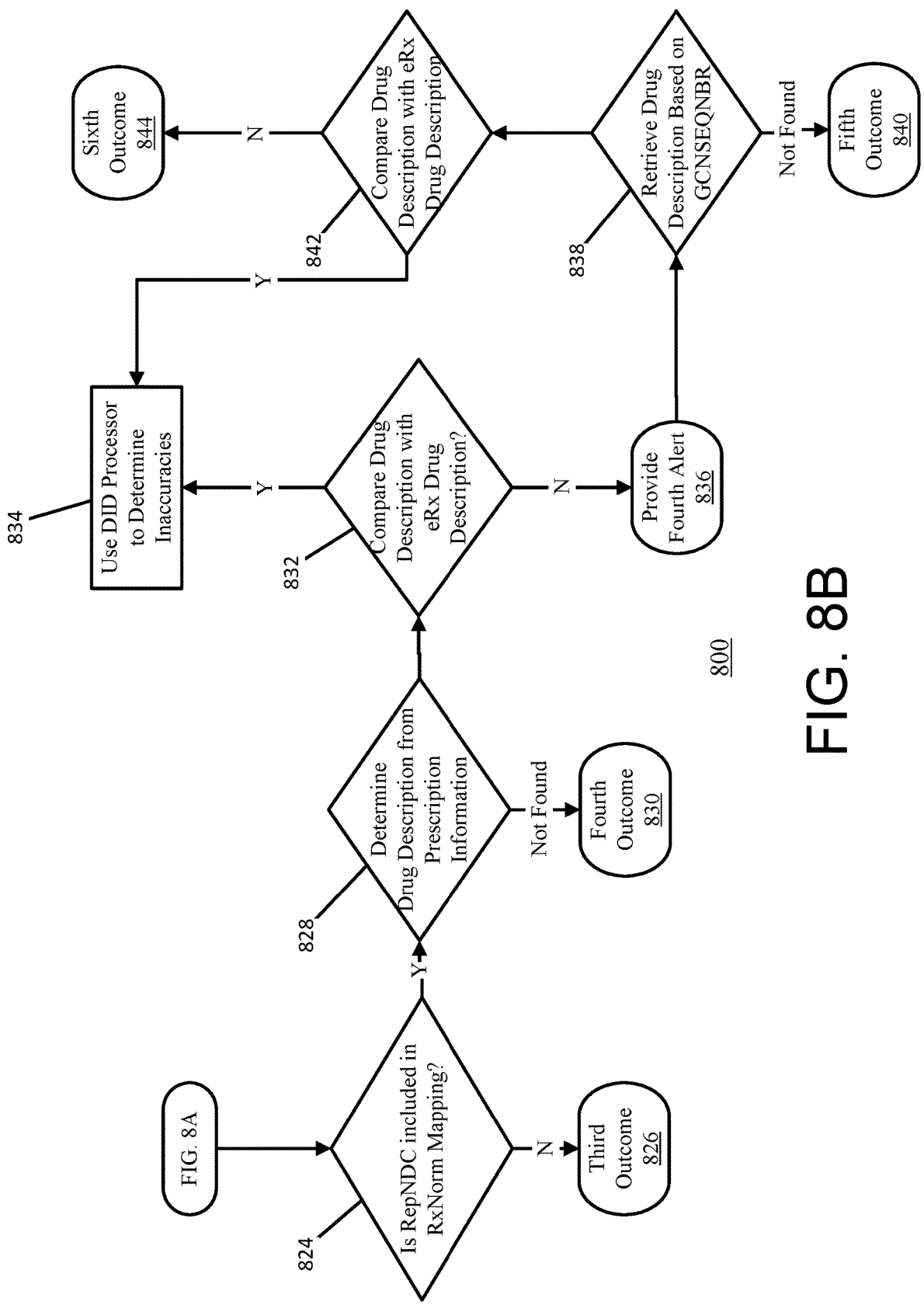

FIGS. 8A and 8B show another exemplary flowchart illustrating another exemplary process 800 for inaccuracy detection and prevention within prescription information in accordance with one or more examples of the present application. The process 800 may be performed by the environment 100 and the exemplary PDVS 106 shown in FIG. 3; however, it will be recognized that any suitable environment and system may be used and that any of the following blocks may be performed in any suitable order. Further, rather than using the pre-defined rules to determine the inaccuracies as described above with reference to the PID processor 312 and/or in traditional systems, the process 800 uses one or more databases (e.g., flat files) to retrieve further information associated with particular aspects from the prescription information such as the NDC code, the RxNorm code, and/or the free-text drug description. Then, the process 800 compares the information from the databases with other information from the databases and/or with the original prescription information to determine whether there are any inaccuracies.

For example, referring to FIG. 8A, at block 802, the PDVS 106 may receive the prescription information (e.g., eRx) for a patient and from a prescriber. As described above, the prescription information may include the medication information (e.g., one or more medication codes/identifiers) and/or a prescription SIG. For instance, the prescription information may include an NDC/repNDC code, a free-text of the drug description, and/or an optional RxNorm code.

At block 804, the PDVS 106 may validate the NDC format from the eRx and check whether the NDC format is valid. If it is valid, then the process 800 proceeds to block 808 and if it is not valid, the process moves to block 806. For example, the PDVS 106 may determine whether the NDC is greater than eleven characters because, as described above, valid NDC codes are ten or eleven characters. The PDVS 106 may further determine whether the NDC includes any non-numeric numbers. Additionally, and/or alternatively, the PDVS 106 may determine if the product code quality is not "ND" ("ND" may be a qualifier that indicates whether the product code is actually an NDC quality code). Based on determining the product quality code is not "ND", the NDC is greater than eleven characters, and/or the NDC code includes non-numeric numbers, the PDVS 106 may determine whether the NDC format is valid or not valid.

In some examples, the PDVS 106 may determine the NDC format is not valid and move to block 806. At block 806, the PDVS 106 may provide a first outcome. An outcome may include recording (e.g., generating) a failure (e.g., the prescription information such as the medication information includes an inaccuracy), stopping the process 800 from continuing, and/or providing a notification (e.g., an outcome message) to the prescription provider system 114 indicating the failure. For example, at block 806, the PDVS 106 may record a failure, stop the process 800 from continuing, and/or provide a notification indicating the NDC code is longer than eleven characters, includes alphabet characters, and/or includes an invalid product code quality (e.g., the product code is not actually an NDC quality code).

At block 808, the PDVS 106 may retrieve a drug code such as a generic product identifier (GPI) code based on the eRx's NDC/repNDC code from a first database. For example, using the eRx's NDC code, the PDVS 106 may query the first database and pull a GPI code from the database. In some instances, the NDC code might not be within the first database. In such instances, the process 800 may move to block 810. Otherwise, after successfully pulling the GPI code from the database, the process 800 may move to block 812. As described above, the GPI code may be used by the DID processor 314 to determine whether there are any dispensing inaccuracies.

At block 810, the PDVS 106 may provide a second outcome. For example, the PDVS 106 may record a failure, stop the process 800 from continuing, and/or provide a notification indicating the eRx's NDC code is not within the first database.

At block 812, the PDVS 106 may determine whether the eRx's prescription information included an RxNorm code. If so, the process 800 proceeds to block 816. Otherwise, the process 800 proceeds to block 814.

At block 814, the PDVS 106 may provide a first alert. An alert may include recording an alert and providing a notification indicating the alert. For example, at block 814, the PDVS 106 may record (e.g., generate) an alert indicating that the RxNorm code was not received as part of the prescription information and provide a notification to the prescription provider system 114 indicating the alert. The process 800 may proceed to block 824 after recording the alert. In some instances, the PDVS 106 may provide the notification indicating the alert immediately after the alert has been generated. In other instances, the PDVS 106 may provide the notification indicating the alert after process 800 and/or process 400 has concluded.

At block 816, the PDVS 106 may check whether the RxNorm format is valid (e.g., validate the RxNorm format). For example, the PDVS 106 may check whether the RxNorm is greater than eight characters. If the RxNorm code is valid, the process 800 may proceed to block 820. Otherwise, the process 800 may proceed to block 818.

At block 818, the PDVS 106 may provide a second alert. For example, the PDVS 106 may record an alert indicating the RxNorm code is longer than eight characters and provide a notification indicating the alert to the prescription provider system 114. After, the process 800 may proceed to block 824 after recording the alert.

At block 820, the PDVS 106 may look-up the RxNorm Code and RxNorm qualifier in a second database (e.g., an RxNorm Crosswalk Database and/or flat file) to determine an NDC code and/or a repNDC code associated with the RxNorm Code. The RxNorm qualifier may indicate whether the medication associated with the RxNorm code is generic or a brand name. The second database may be an RxNorm Crosswalk Database (e.g., a schema crosswalk that maps elements in one schema to equivalent elements in another schema) that is stored in the PDVS 106 and/or the DID processor 314. The PDVS 106 may use the second database to retrieve information (e.g., drug names, NDCs, and/or other information) that corresponds to the information from the eRx. For example, at block 820, the PDVS 106 may retrieve one or more NDCs (e.g., database NDCs) from the second database based on the RxNorm from the eRx. In other words, within the second database, the particular RxNorm from the eRx may be associated with one or more database NDCs and at block 820, the PDVS 106 may pull/retrieve these database NDCs using the eRx's RxNorm.

In some examples, the first and second database may be the same database. For instance, the PDVS 106 may retrieve the drug code associated with the eRx's NDC as well as retrieve the database NDCs associated with the RxNorm codes from the same database (e.g., same flat file).

In some instances, the PDVS 106 may determine that there are no database NDCs associated with the eRx's RxNorm. In such instances, the process 800 may move to block 822. Otherwise, if the PDVS 106 determines at least one database NDC for the RxNorm code, the process 800 may move to block 824.

At block 822, the PDVS 106 may provide a third alert. For example, the PDVS 106 may record an alert indicating that there is no return information within the second database and provide a notification indicating the alert to the prescription provider system 114. After, the process 800 may proceed to block 824 after recording the alert.

Referring to FIG. 8B, at block 824, the PDVS 106 may determine whether the eRx's NDC and/or repNDC is included in the database NDCs from the RxNorm mapping. For example, the PDVS 106 may use the results from block 820 (e.g., the retrieved database NDCs associated with the eRx's RxNorm codes) to determine whether the eRx's NDC/repNDC matches any of the retrieved database NDCs. Based on the eRx's NDC/repNDC matching the database NDCs, the process 800 moves to block 828. Otherwise, the process moves to block 826.

Additionally, and/or alternatively, the eRx might not include an RxNorm code, the RxNorm code might not be valid, and/or the PDVS 106 might not find any database NDCs associated with the eRx's RxNorm. In such examples, the PDVS 106 might not be able to retrieve any database NDCs associated with eRx's RxNorm. As such, the PDVS 106 may compare the eRx's NDC/repNDC with the NDCs/repNDCs stored within the second database to determine whether the eRx's NDC/repNDC is within the second database. If so, the process 800 may also move to block 828.

At block 826, the PDVS 106 may provide a third outcome. For example, the PDVS 106 may record (e.g., generate) a failure, stop process 800, and/or provide a notification indicating the failure such as the eRx's NDC is not included in the RxNorm mapping and/or within the second database.

At block 828, using the second database, the PDVS 106 may determine a database drug description associated with the eRx's NDC code and/or the database NDCs associated with the eRx's RxNorm. For instance, the second database may further include drug names (e.g., a free-text description of the drug) that are associated with different RxNorms, NDCs, and/or generic code number sequence numbers (GCNSEQNBR). For instance, using the second database, the PDVS 106 may retrieve a database drug description such as "amoxicillin" based on the RxNorm, NDC (e.g., eRx's NDC and/or the database NDC), and/or the GCNSEQNBR. In some instances, the PDVS 106 might not be able to retrieve a database drug description associated with the eRx's NDC code and/or the database NDCs. In such instances, the process 800 may move to block 830. Based on the PDVS 106 retrieving a database drug description, the process 800 may move to block 832.

At block 830, the PDVS 106 may provide a fourth outcome. For example, the PDVS 106 may record (e.g., generate) a failure, stop process 800, and/or provide a notification indicating the failure such as being unable to find the drug name in the second database.

At block 832, the PDVS 106 may compare the database drug description associated with the eRx's NDC code and/or database NDCs with the drug description from the eRx from the prescriber. For instance, the PDVS 106 may isolate the first word (e.g., up to a space or special character) and/or additional words within the name and check for it within the drug description from the prescriber. In other words, after retrieving the drug description from the second database, the PDVS 106 may compare this drug description with the drug description from the prescriber to check whether it matches. If it matches, then the process moves to block 834. If it does not match, then the process moves to block 836.

At block 834, the PDVS 106 may pass (e.g., provide/transmit) the drug code (e.g., the GPI) from block 808 to the DID processor 314. The DID processor 314 may use the GPI/drug code to determine whether there are any dispensing inaccuracies and/or other inaccuracies within the prescription information, which is described above.

At block 836, the PDVS 106 may provide a fourth alert. For example, the PDVS 106 may record an alert indicating that the database drug description from the second database was not found and/or does not match in the drug description from the eRx and provide a notification indicating the alert to the prescription provider system 114. After, the process 800 may proceed to block 838 after recording the alert.

At block 838, the PDVS 106 may retrieve a database drug description associated with the GCNSEQNBR. For instance, the second database may include information indicating GCNSEQNBRs based on the eRx's NDC/repNDC. The PDVS 106 may use the second database to retrieve one or more GCNSEQNBRs based on the eRx's NDC/repNDC. Then, using the retrieved GCNSEQNBRs, the PDVS 106 may retrieve a database drug description associated with the retrieved GCNSEQNBRs. If the GCNSEQNBR is not found within the second database, then the process 800 may move to block 840. Otherwise, the process 800 may move to block 842.

At block 840, the PDVS 106 may provide a fifth outcome. For example, the PDVS 106 may record (e.g., generate) a failure, stop process 800, and/or provide a notification indicating the failure such as being unable to find the GCNSEQNBR within the second database.

At block 842, the PDVS 106 may compare the database drug description associated with the GCNSEQNBR with the drug description from the eRx. This block may operate similarly to block 832. For instance, the PDVS 106 may compare one or more words within the database drug description (e.g., up to a space or special character) and check for it within the eRx's drug description. If it is found within the eRx's drug description, then the process 800 may move to block 834, which is described above. Otherwise, the process 800 may move to block 844.

At block 844, the PDVS 106 may provide a sixth outcome. For example, the PDVS 106 may record (e.g., generate) a failure, stop process 800, and/or provide a notification indicating the drug name is not find in the drug description.

In some examples, the DID processor 314 (e.g., a dedicated engine within the DID processor 314) may perform the process 800 as described above. In other examples, another processor, including a separate processor that is operating in parallel to the parsing processor 308, may perform the process 800. For example, the separate processor may receive information such as the prescription information from the routing system 302, perform process 800, and/or provide the outcomes/alerts to the DID processor 314, the decollision processor 318, and/or another processor within the PDVS 106.

In some instances, the process 800 may be performed during process 400 (e.g., in-between two steps of process 400) and/or may be performed in parallel with process 400. For instance, the process 800 may be performed after block 402 (e.g., after receiving the prescription information from the prescriber) and prior to block 404 (e.g., prior to converting the prescription information into hierarchical prescription entries). In other instances, the process 800 may be performed after block 404 (e.g., after converting the prescription information into hierarchical prescription entries) and prior to block 406 (e.g., determining whether the hierarchical prescription entries includes one or more dispensing inaccuracies).

It will be appreciated that the figures of the present application and their corresponding descriptions are merely exemplary, and that the application is not limited to these exemplary situations.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

It will be appreciated that the examples of the application described herein are merely exemplary. Variations of these examples may become apparent to those of ordinary skill in the art upon reading the foregoing description. The inventors expect skilled artisans to employ such variations as appropriate, and the inventors intend for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

The invention claimed is:

1. A method, comprising:
receiving, by a prescription determination and verification system (PDVS) and from a prescription generation system, prescriber prescription information indicating an electronically transmitted medical prescription associated with a patient;

converting, by the PDVS, the electronically transmitted prescription information to a plurality of hierarchical prescription entries based on parsing the electronically transmitted medical prescription associated with the patient;

determining, by the PDVS, whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries;

based on determining the one or more dispensing inaccuracies within the plurality of hierarchical prescription entries, providing, by the PDVS and to a prescription provider system, provider prescription information indicating the converted electronically transmitted prescription information and the one or more dispensing inaccuracies;

in response to providing the provider prescription information, receiving, by the PDVS and from the prescription provider system, disposition data indicating a response to the one or more dispensing inaccuracies;

training, by the PDVS, one or more machine learning (ML)-artificial intelligence (AI) algorithms using the disposition data indicating the response to the one or more dispensing inaccuracies; and determining, by the PDVS, one or more new dispensing inaccuracies associated with a new electronically transmitted medical prescription based on using the one or more trained ML-AI algorithms.

2. The method of claim 1, further comprising:
updating the one or more dispensing parameters based on the disposition information.

3. The method of claim 1, wherein determining whether the hierarchical prescription entries includes the one or more dispensing inaccuracies is based on performing a sequential comparative analysis using the hierarchical prescription entries and the rankings associated with the plurality of hierarchical prescription entries.

4. The method of claim 1, wherein the PDVS comprises a first processor, a second processor, and a third processor,
wherein determining whether the plurality of hierarchical prescription entries includes the one or more dispensing inaccuracies comprises determining, by the first processor, whether the plurality of hierarchical prescription entries includes the one or more dispensing inaccuracies, wherein the one or more dispensing inaccuracies are introduced by a dispensing system, and wherein the method further comprises:
determining, by the second processor, whether the plurality of hierarchical entries includes one or more prescriber inaccuracies, wherein the one or more prescriber inaccuracies are introduced by the prescriber generation system; and
determining, by the third processor, whether the plurality of hierarchical entries includes one or more financial inaccuracies.

5. The method of claim 4, wherein the PDVS comprises a decollisioning processor, and wherein the method further comprises:
determining, by the decollisioning processor, priorities between the one or more dispensing inaccuracies, the one or more prescriber inaccuracies, and the one or more financial inaccuracies, and wherein providing the one or more dispensing inaccuracies is based on the determined priorities.

6. The method of claim 1, wherein converting the electronically transmitted prescription information to the plurality of hierarchical prescription entries is based on using a natural language processing (NLP) machine learning algorithm.

7. The method of claim 1, wherein the prescriber prescription information comprises medication information and a prescription signa, wherein the medication information indicates one or more identifiers associated with a medication for the patient, and wherein the prescription signa indicates directions for the patient to take the medication.

8. The method of claim 7, wherein converting the electronically transmitted prescription information to the plurality of hierarchical prescription entries comprises generating a first subset of hierarchical prescription entries, of the plurality of hierarchical prescription entries, associated with the medication information and a second subset of the hierarchical entries, of the plurality of hierarchical prescription entries, associated with the prescription signa,
wherein the ranking indicates that the first subset of hierarchical prescription entries is ranked higher than the second subset of hierarchical entries.

9. The method of claim 7, wherein the medication information comprises a national drug code (NDC) and a free-text entry describing the medication, and
wherein the method further comprises:
retrieving, from a database, a database drug description based on the NDC; and
comparing whether the database drug description matches the free-text entry describing the medication.

10. The method of claim 9, wherein the medication information further comprises an RxNorm code, and
wherein the method further comprises:
retrieving, from the database, a database NDC based on the RxNorm code; and
comparing the database NDC with the NDC from the medication information.

11. The method of claim 9, wherein the method further comprises:
retrieving, from the database, a generic code number sequence number (GCNSEQNBR) based on the NDC;
retrieving, from the database, a second database drug description based on the retrieved GCNSEQNBR; and
comparing whether the second database drug description matches the free-text entry describing the medication.

12. The method of claim 9, wherein the method further comprises:
retrieving, from a second database, a generic product identifier (GPI) based on the NDC, and
wherein the converting the electronically transmitted prescription information to the plurality of hierarchical prescription entries is further based on the GPI.

13. A system, comprising:
one or more processors; and
a non-transitory computer-readable medium having processor-executable instructions stored thereon, wherein the processor-executable instructions, when executed, facilitate:
receiving, from a prescription generation system, prescriber prescription information indicating an electronically transmitted medical prescription associated with a patient;

converting the electronically transmitted prescription information to a plurality of hierarchical prescription entries based on parsing the electronically transmitted medical prescription associated with the patient;

determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries;

based on determining the one or more dispensing inaccuracies within the plurality of hierarchical prescription entries, providing, to a prescription provider system, provider prescription information indicating the converted electronically transmitted prescription information and the one or more dispensing inaccuracies;

in response to providing the provider prescription information, receiving, from the prescription provider system, disposition data indicating a response to the one or more dispensing inaccuracies;

training one or more machine learning (ML)-artificial intelligence (AI) algorithms using the disposition data indicating the response to the one or more dispensing inaccuracies; and determining one or more new dispensing inaccuracies associated with a new electronically transmitted medical prescription based on using the one or more trained ML-AI algorithms.

14. The system of claim 13, wherein the processor-executable instructions, when executed, further facilitate:

updating the one or more dispensing parameters based on the disposition information.

15. The system of claim 13, wherein determining whether the hierarchical prescription entries includes the one or more dispensing inaccuracies is based on performing a sequential comparative analysis using the hierarchical prescription entries and the rankings associated with the plurality of hierarchical prescription entries.

16. A non-transitory computer-readable medium having processor-executable instructions stored thereon, wherein the processor-executable instructions, when executed, facilitate:

receiving, from a prescription generation system, prescriber prescription information indicating an electronically transmitted medical prescription associated with a patient;

converting the electronically transmitted prescription information to a plurality of hierarchical prescription entries based on parsing the electronically transmitted medical prescription associated with the patient;

determining whether the plurality of hierarchical prescription entries includes one or more dispensing inaccuracies based on using the plurality of hierarchical prescription entries, the prescriber prescription information, and one or more dispensing parameters indicating a ranking associated with the plurality of hierarchical prescription entries;

based on determining the one or more dispensing inaccuracies within the plurality of hierarchical prescription entries, providing, to a prescription provider system, provider prescription information indicating the converted electronically transmitted prescription information and the one or more dispensing inaccuracies;

in response to providing the provider prescription information, receiving, from the prescription provider system, disposition data indicating a response to the one or more dispensing inaccuracies;

training one or more machine learning (ML)-artificial intelligence (AI) algorithms using the disposition data indicating the response to the one or more dispensing inaccuracies; and determining one or more new dispensing inaccuracies associated with a new electronically transmitted medical prescription based on using the one or more trained ML-AI algorithms.

* * * * *